(12) United States Patent
Ma et al.

(10) Patent No.: US 11,359,191 B2
(45) Date of Patent: Jun. 14, 2022

(54) VARIANT RECOMBINANT DERMATOPHAGOIDES PTERONYSSINUS TYPE 1 ALLERGEN PROTEIN AND ITS PREPARATION METHOD AND APPLICATION

(71) Applicant: ZONHON BIOPHARMA INSTITUTE,INC, Jiangsu (CN)

(72) Inventors: Bruce Yong Ma, Jiangsu (CN); Yu Fan, Jiangsu (CN); Anliang Wang, Jiangsu (CN); Jun Wang, Jiangsu (CN)

(73) Assignee: ZONHON BIOPHARMA INSTITUTE, INC

( * ) Notice: Subject to any disclaimer, the term of this patent is extended or adjusted under 35 U.S.C. 154(b) by 286 days.

(21) Appl. No.: 16/474,240

(22) PCT Filed: Dec. 28, 2017

(86) PCT No.: PCT/CN2017/119184
§ 371 (c)(1),
(2) Date: Jun. 27, 2019

(87) PCT Pub. No.: WO2018/121637
PCT Pub. Date: Jul. 5, 2018

(65) Prior Publication Data
US 2020/0123523 A1    Apr. 23, 2020

(30) Foreign Application Priority Data

Dec. 31, 2016 (CN) .......................... 201611270412.2

(51) Int. Cl.
*C12N 9/64* (2006.01)
*A61K 39/35* (2006.01)
*C12N 15/81* (2006.01)

(52) U.S. Cl.
CPC .............. *C12N 9/641* (2013.01); *A61K 39/35* (2013.01); *C12N 15/815* (2013.01); *C12Y 304/22065* (2013.01)

(58) Field of Classification Search
CPC ...................................................... C12N 9/641
USPC .......................................................... 435/212
See application file for complete search history.

(56) References Cited

U.S. PATENT DOCUMENTS

2011/0293665 A1    12/2011 Bordas et al.
2015/0152148 A1    6/2015 Asturias Ortega et al.

FOREIGN PATENT DOCUMENTS

CN    102732541 A    10/2012
CN    105307679 A    2/2016

OTHER PUBLICATIONS

Coetzee et al, Influence of codon optimization, promoter, and strain selection on the heterologous production of a β-fructofuranosidase from Aspergillus fijiensis ATCC 20611 in Pichia pastoris. Folia Microbiologica Feb. 8, 2022 12 pages.*
Asturias, J. A. "Registration No. FM177224.1, Dermatophagoides pteronyssinus mRNAfor Derp 1 allergen (derp1 gene)" GenBank Database. Jul. 24, 2016 (Jul. 24, 2016), see nucleotide.
De Halleux, S. et al., Chain A, Crystal Structure of Mature And Fully Active Der P 1 Allergen, J. Allergy Clin. Immunol., Aug. 23, 2005, pp.
International Search Report and Written Opinion in PCT/CN2017/119184 dated Mar. 30, 2018.

* cited by examiner

*Primary Examiner* — Sheridan Swope
(74) *Attorney, Agent, or Firm* — Dilworth IP, LLC

(57) ABSTRACT

A DNA sequence encoding Der p1 protein having a particular base sequence is codon-optimized for the *Pichia pastoris* expression system, which is conducive to expressing Der p1 in *Pichia pastoris*. After gene optimization and adding an activating element to increase the expression of Der p1 in molecular level, it was found that Der p1 is expressed at a higher level as compared with the prior art and has biological activity similar to the natural protein.

4 Claims, 15 Drawing Sheets
Specification includes a Sequence Listing.

Figure 1

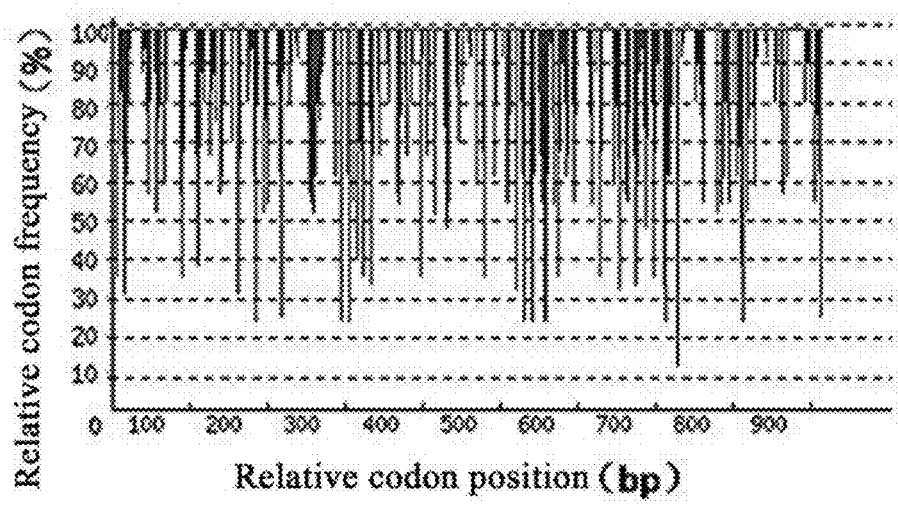
Figure 2-a
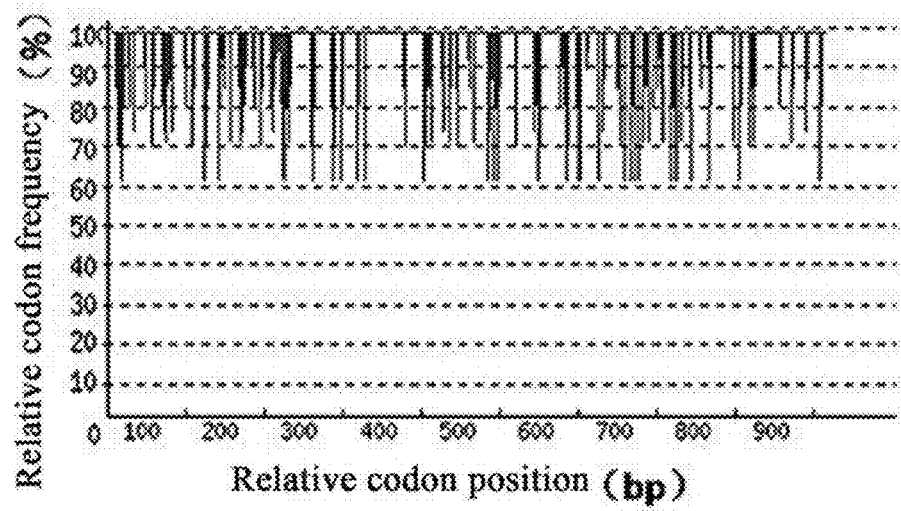
Figure 2-b
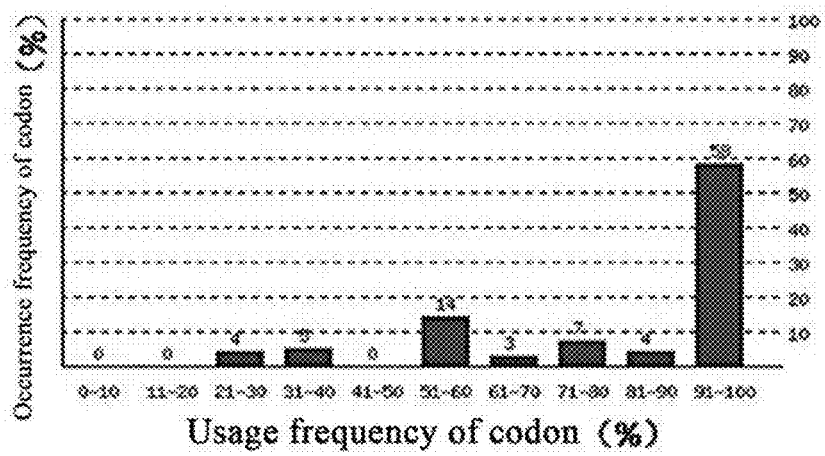
Figure 3-a

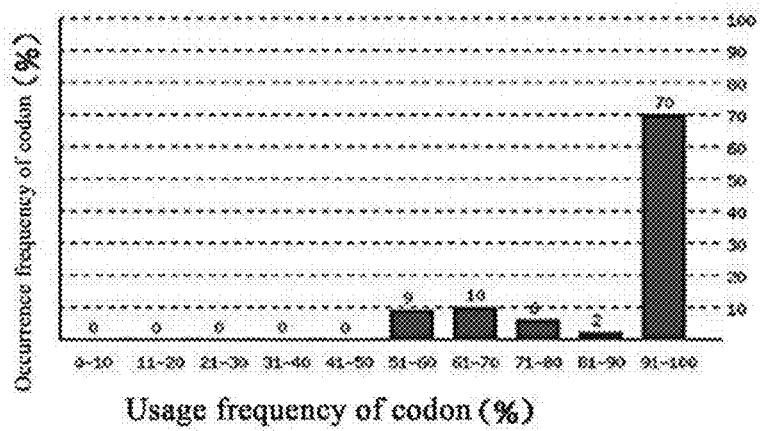
Figure 3-b
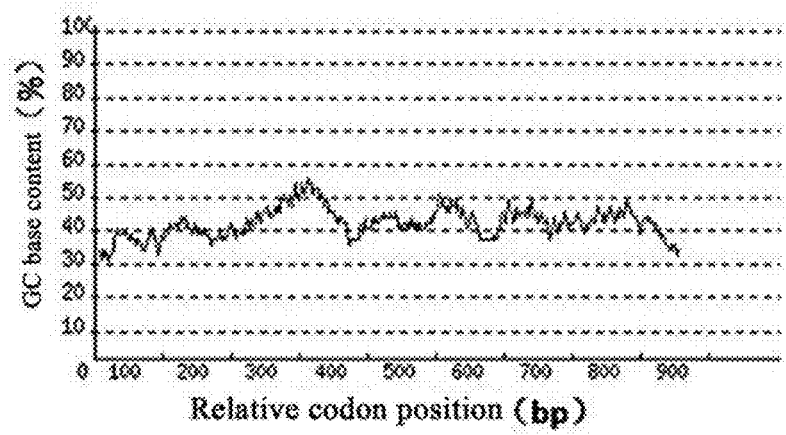
Figure 4-a
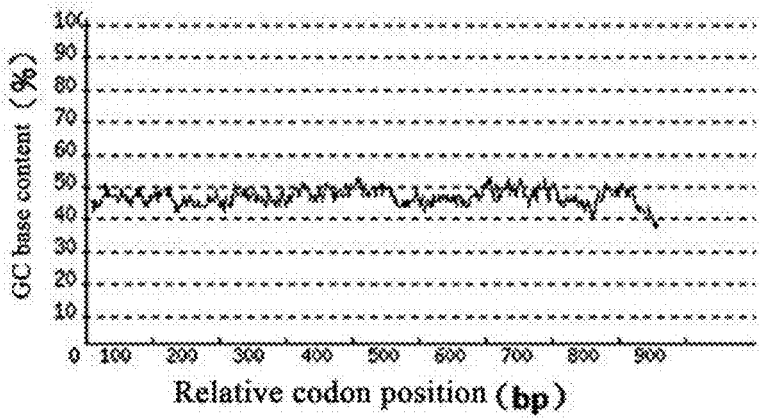
Figure 4-b

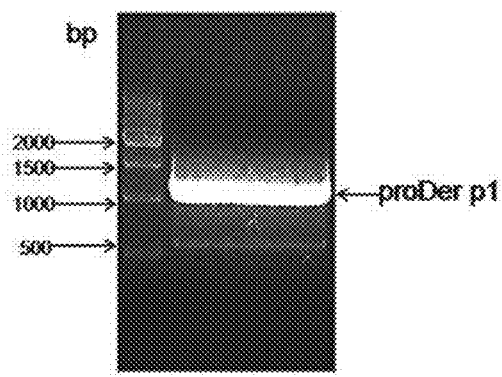
Figure 5
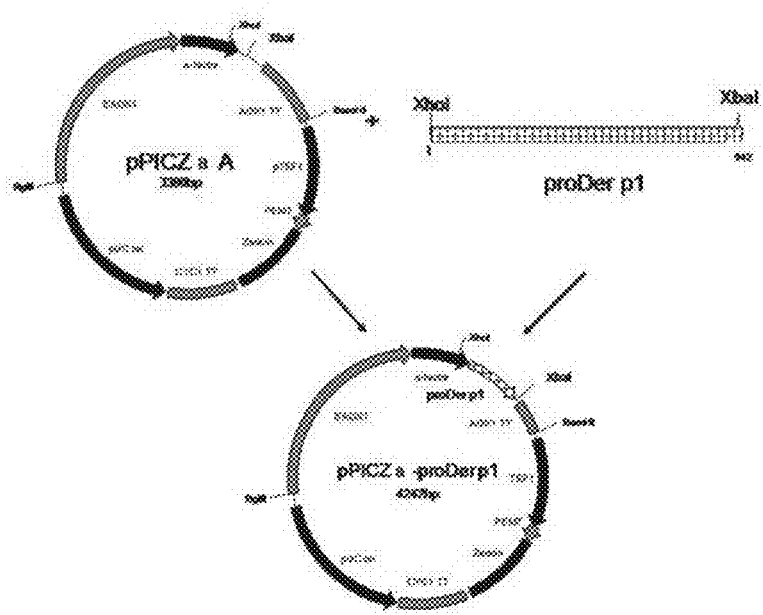
Figure 6
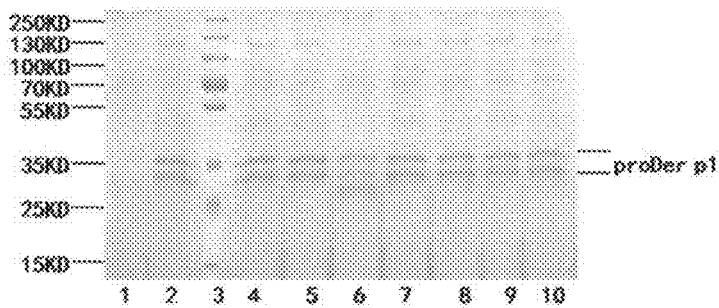
Figure 7-a

Figure 7-b
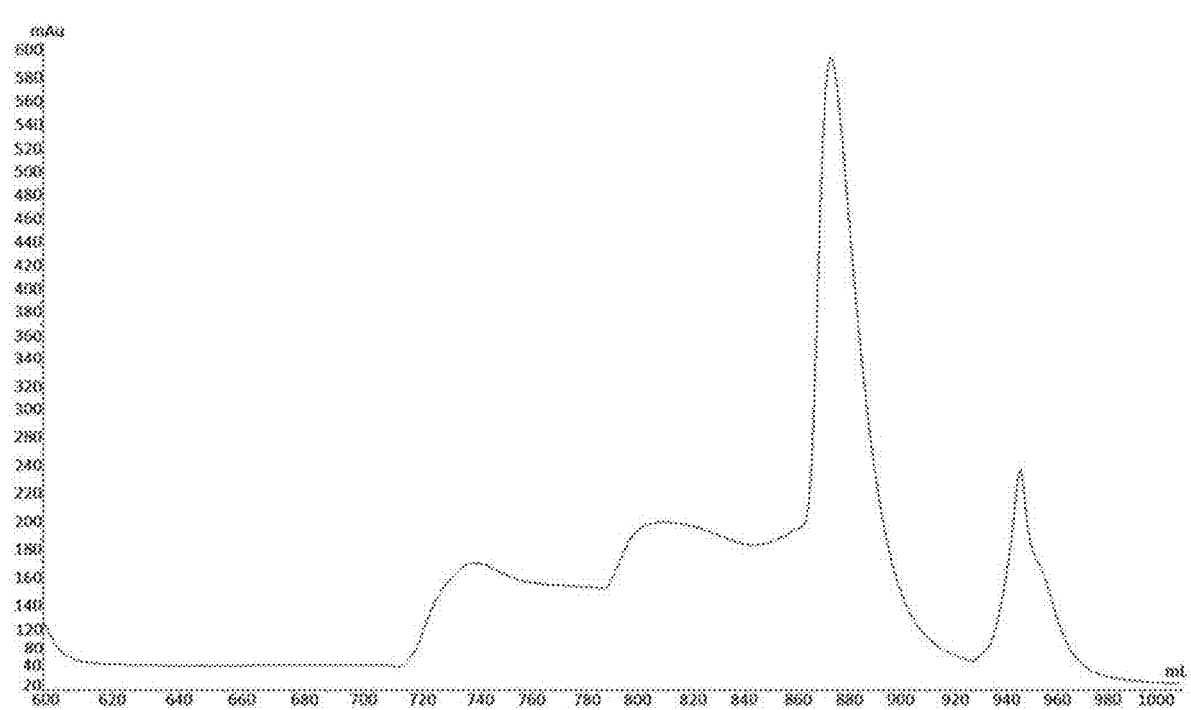
Figure 8-a
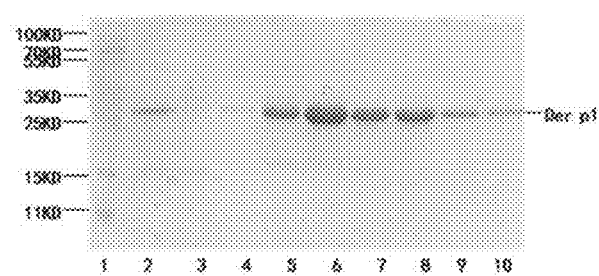
Figure 8-b

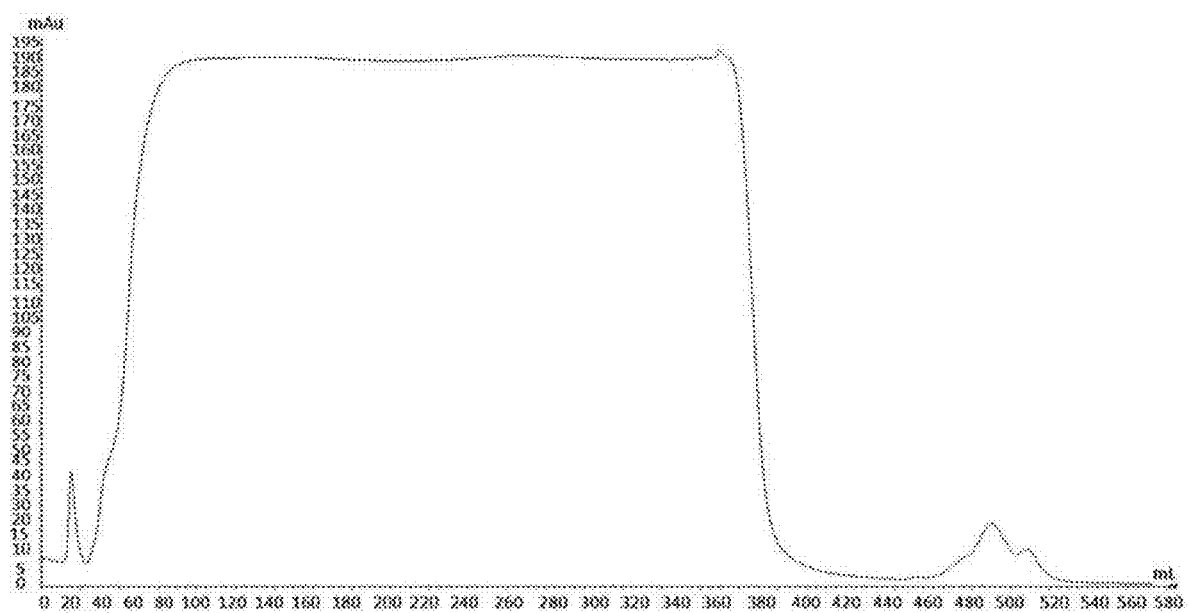
Figure 9-a
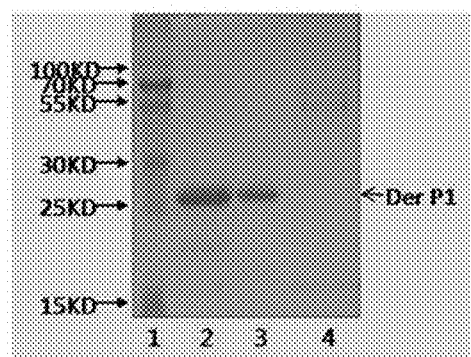
Figure 9-b
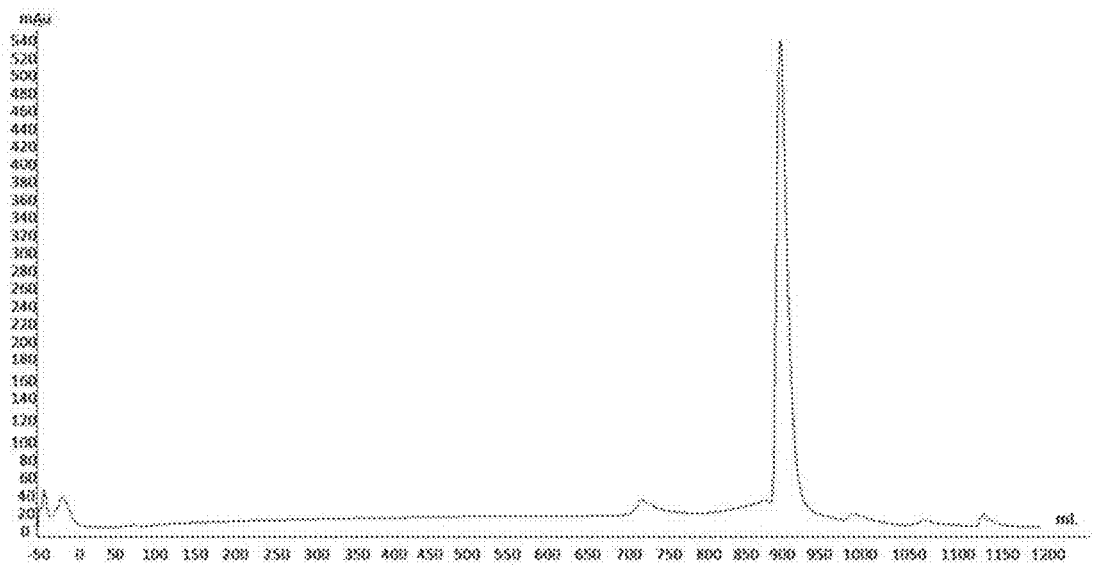
Figure 10-a

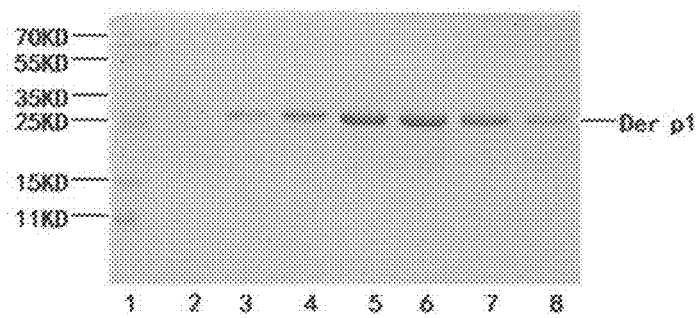
Figure 10-b
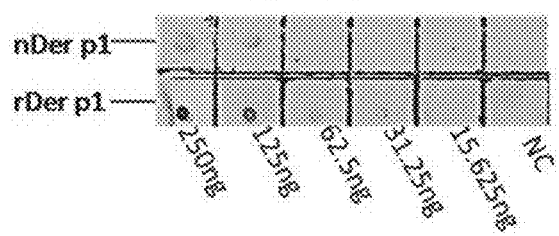
Figure 11
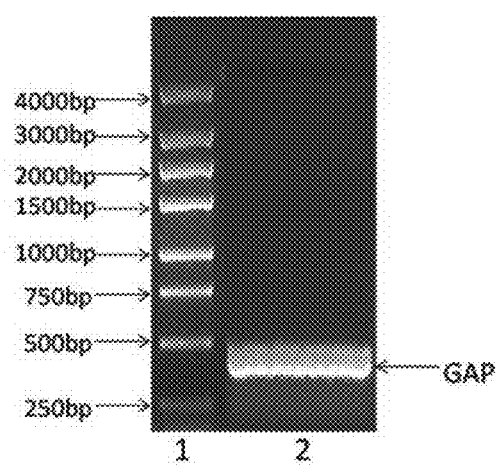
Figure 12
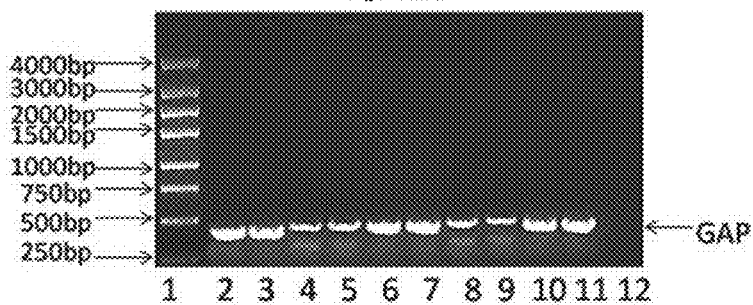
Figure 13

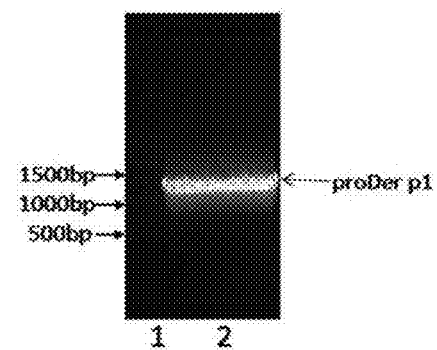
Figure 14
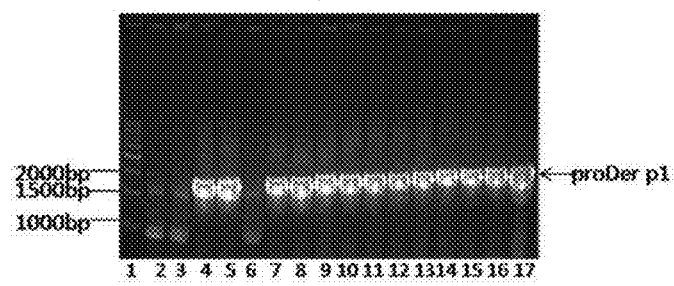
Figure 15
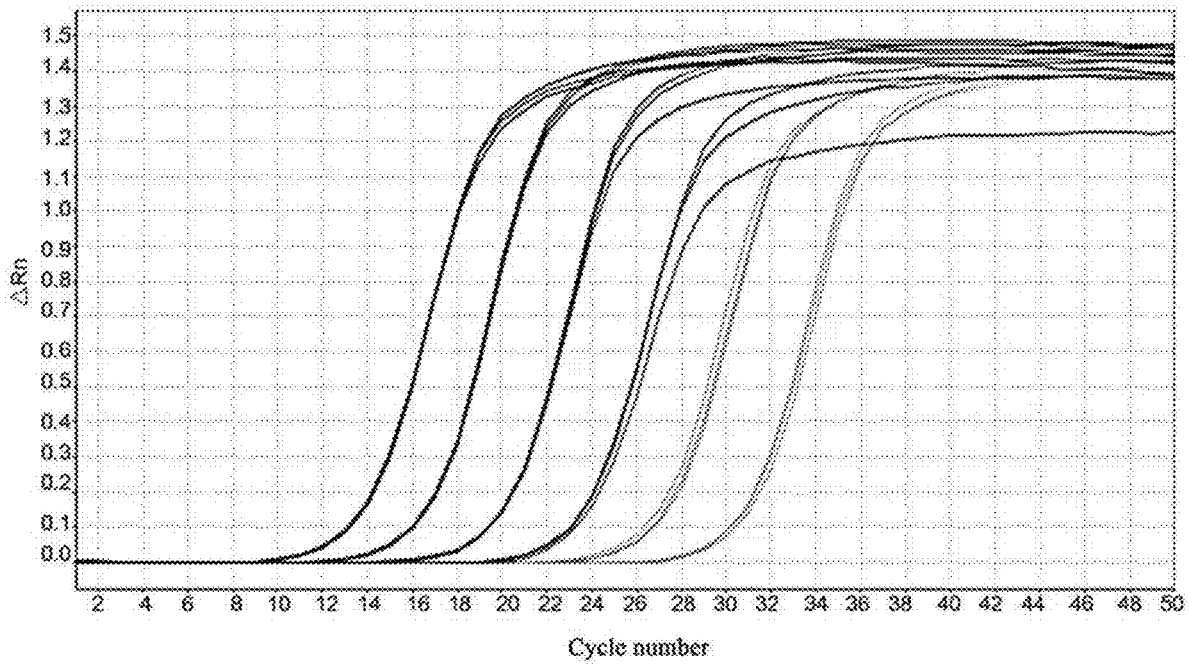
Figure 16-a

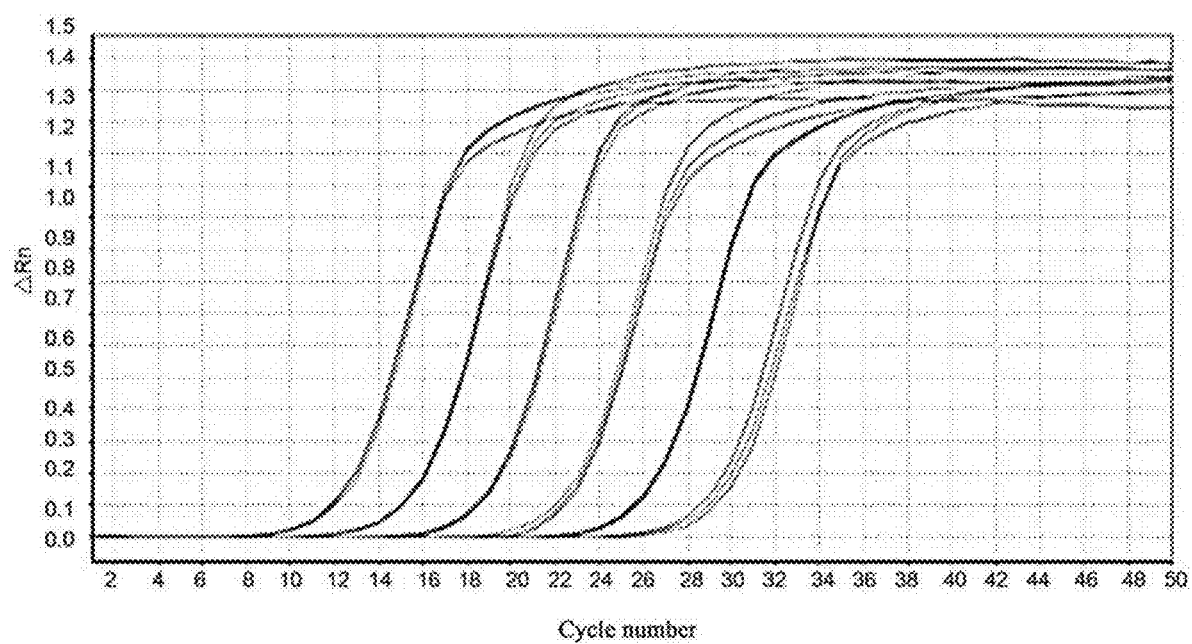
Figure 16-b

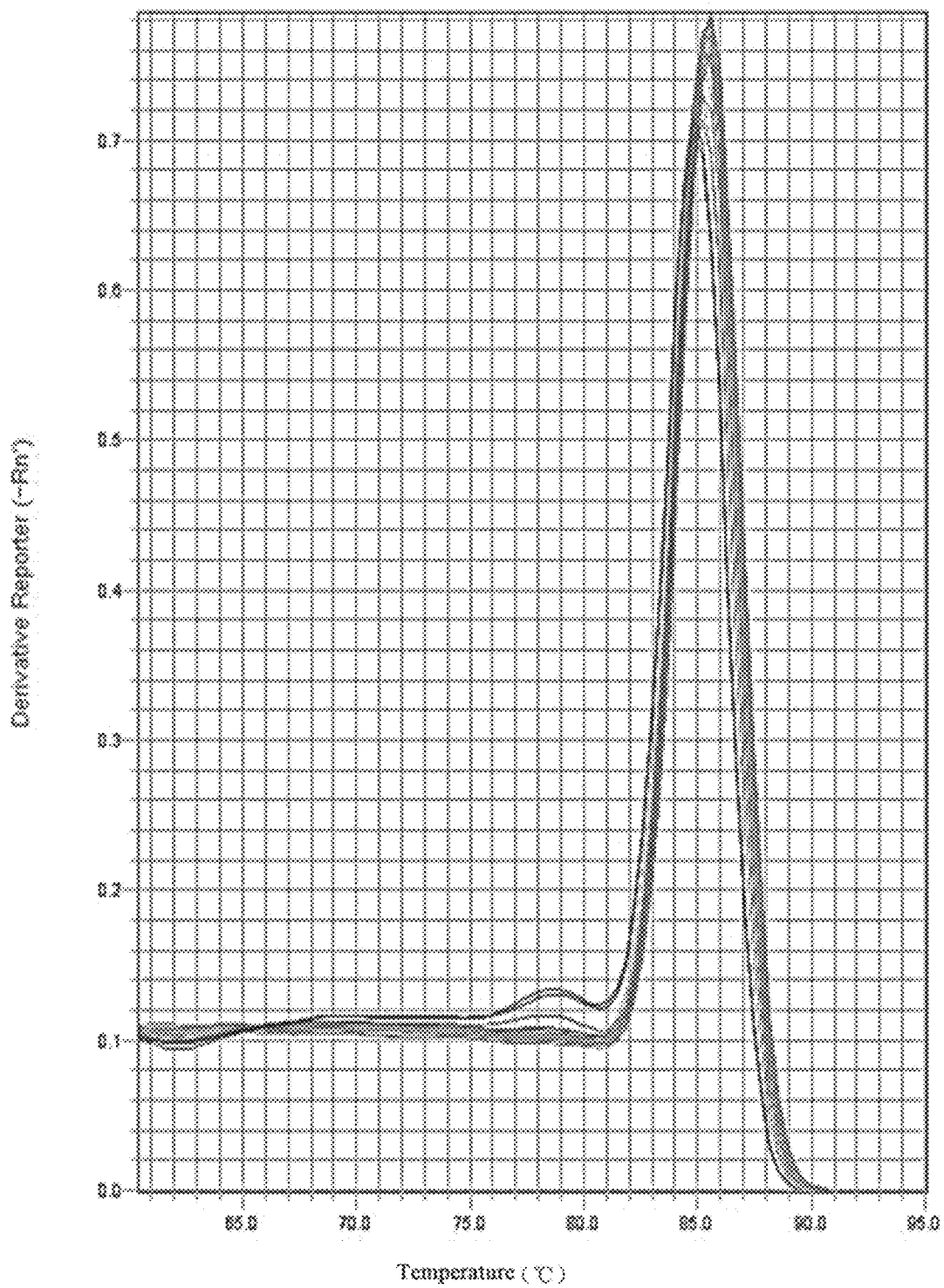
Figure 17-a

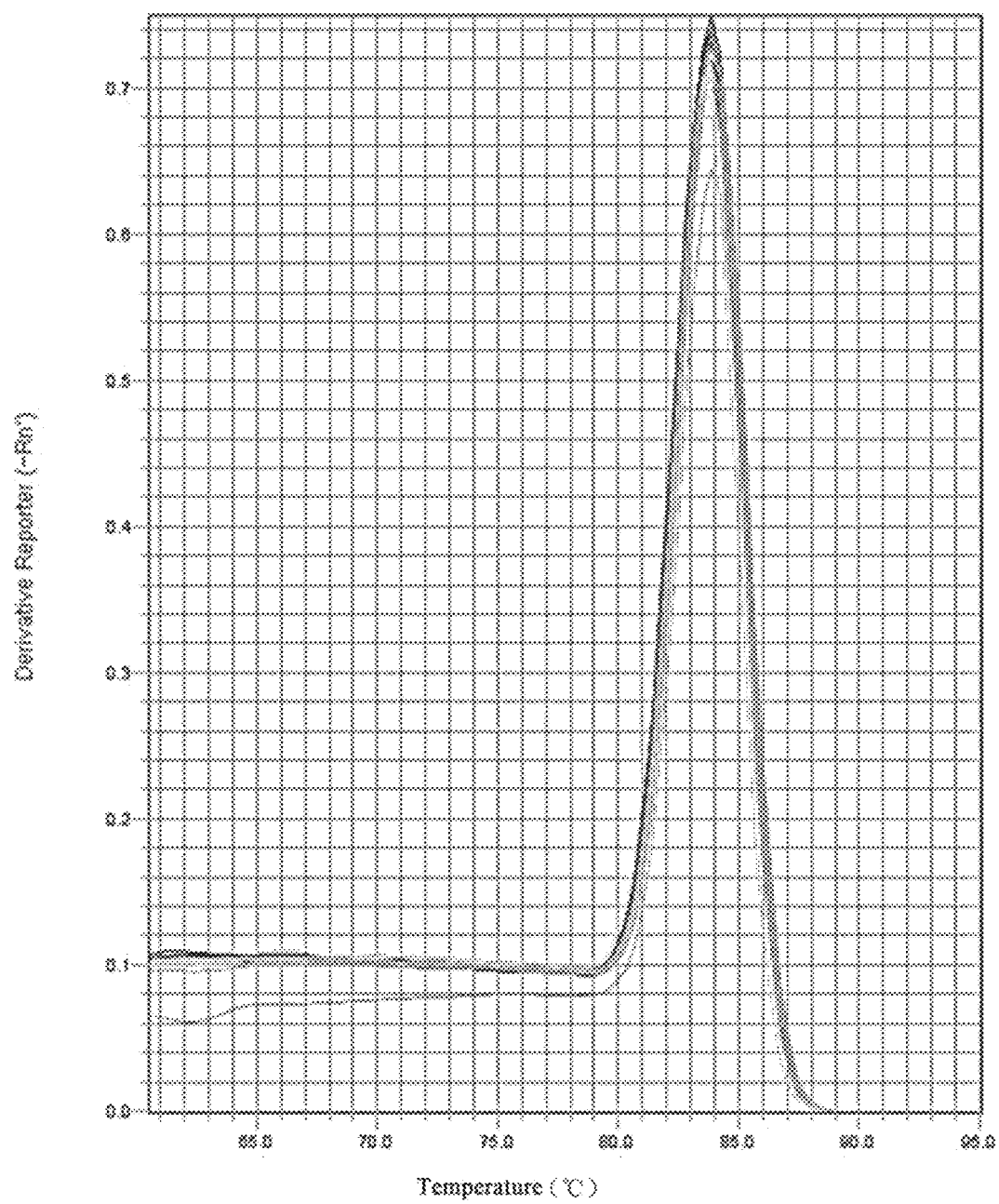
Figure 17-b

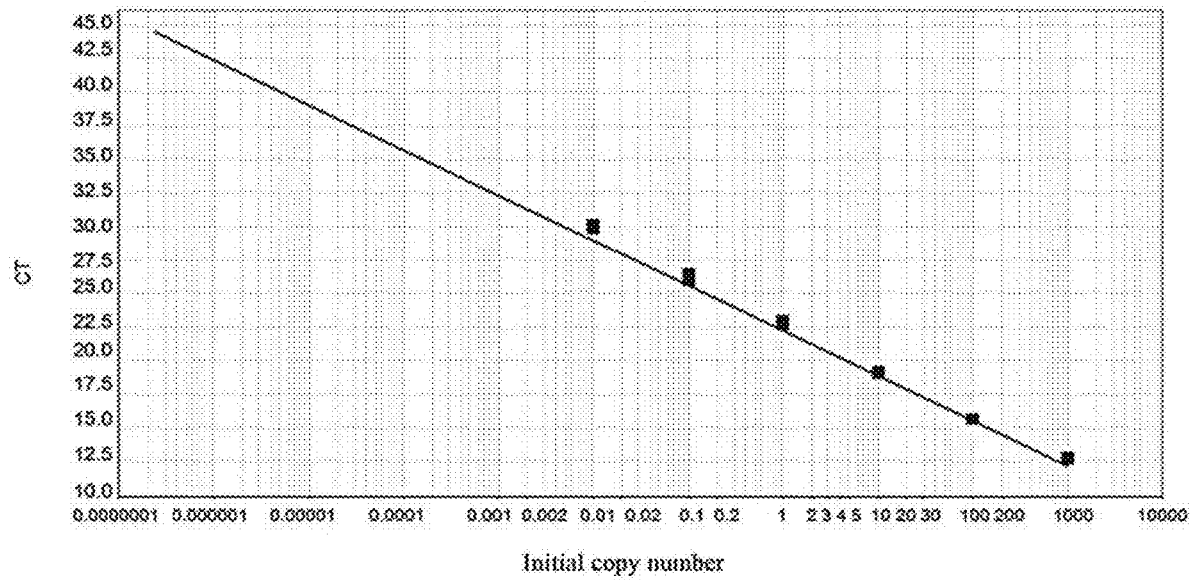
Figure 18-a
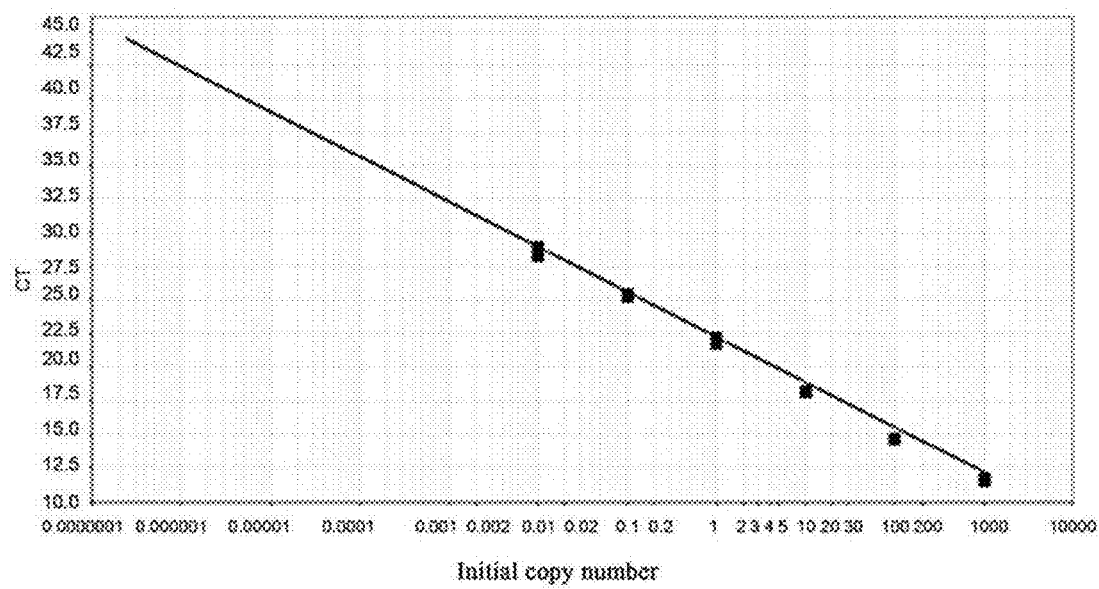
Figure 18-b

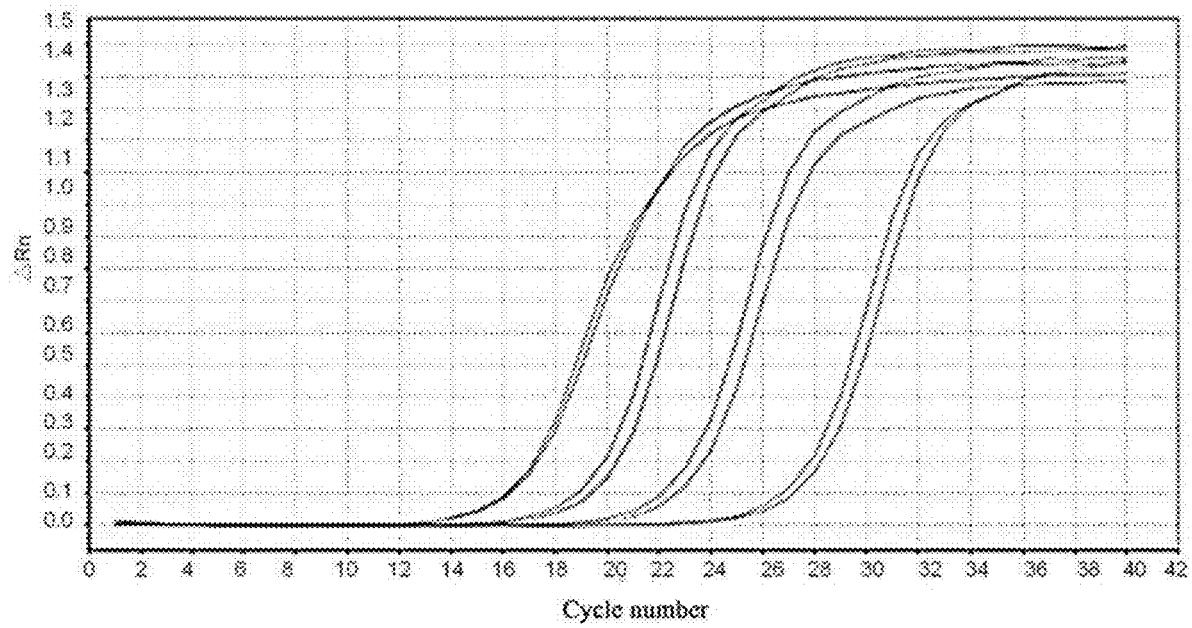
Figure 19-a
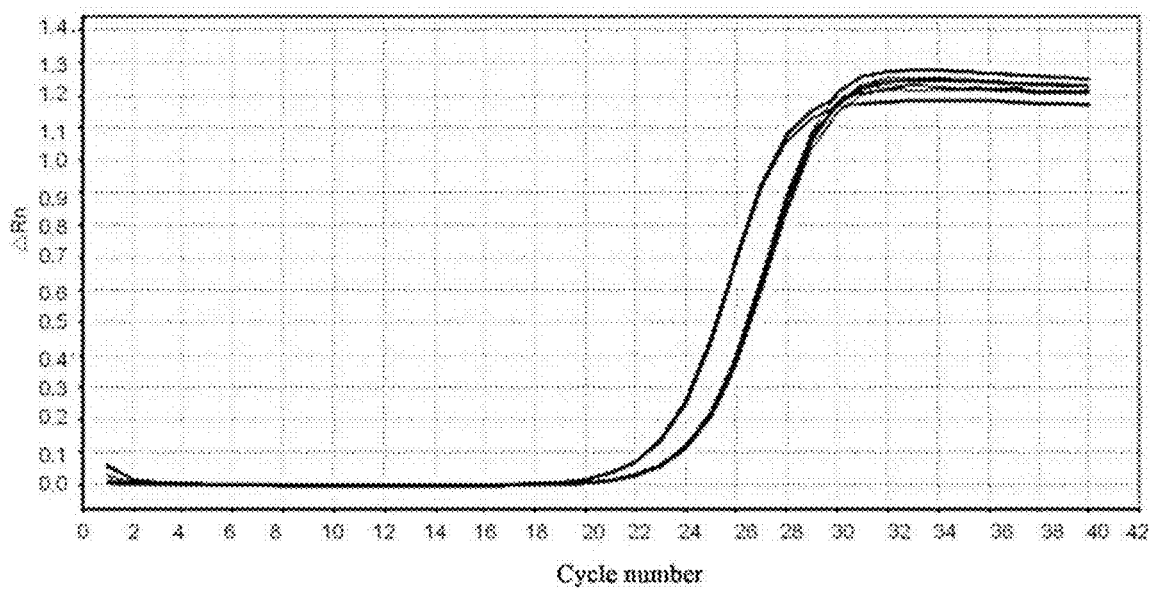
Figure 19-b

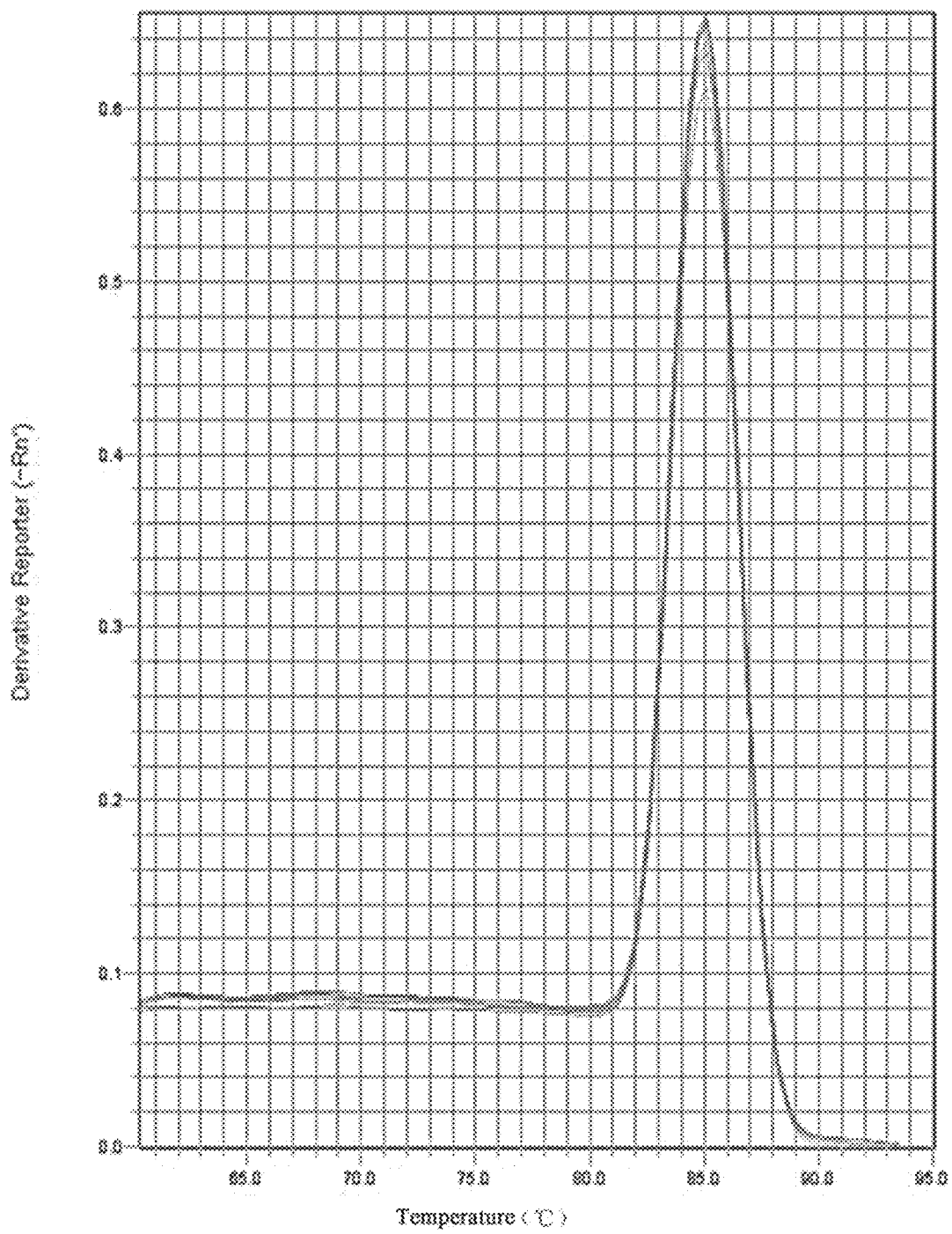
Figure 20-a

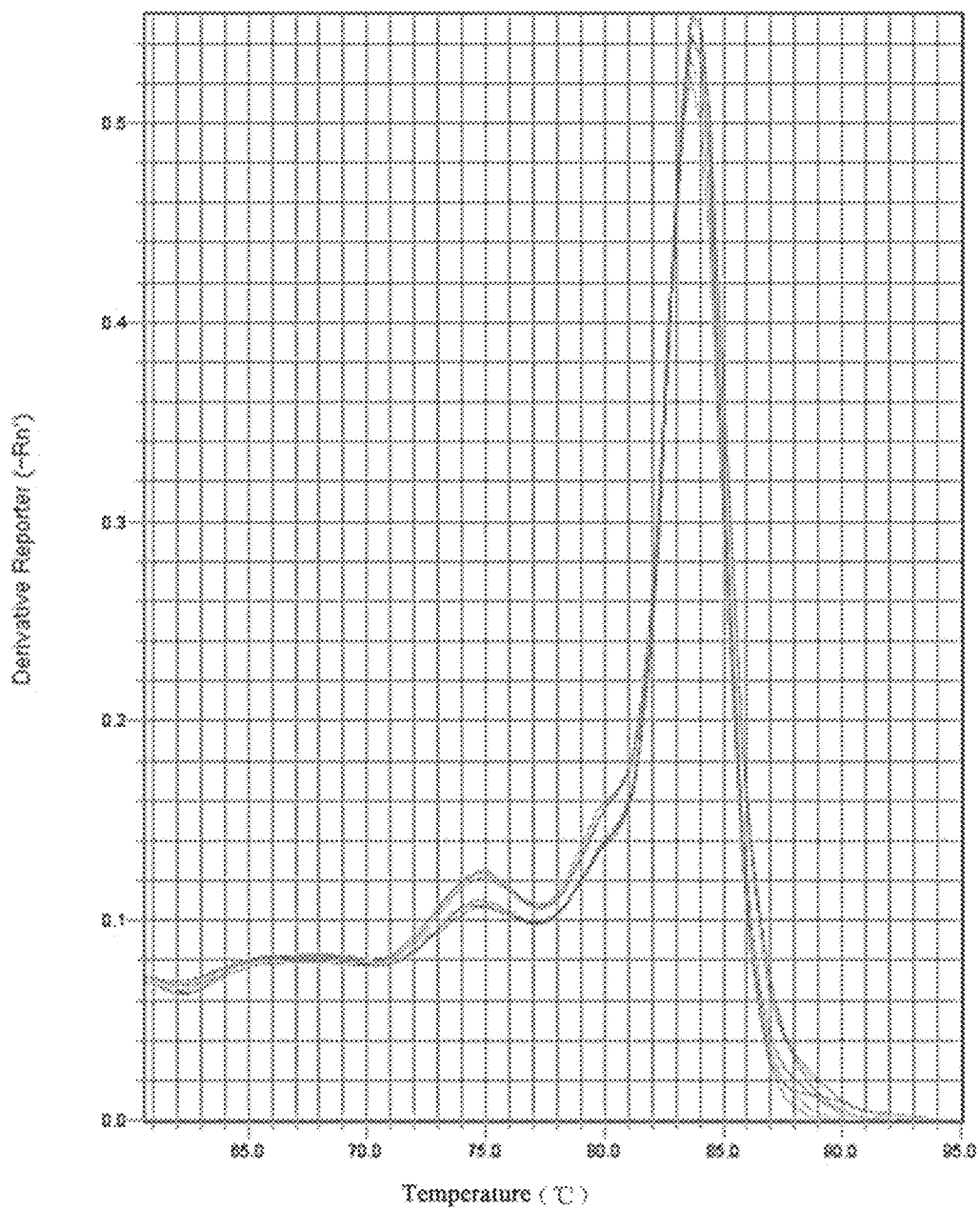
Figure 20-b

VARIANT RECOMBINANT DERMATOPHAGOIDES PTERONYSSINUS TYPE 1 ALLERGEN PROTEIN AND ITS PREPARATION METHOD AND APPLICATION

SEQUENCE LISTING

The instant application contains a Sequence Listing which has been filed electronically in ASCII format and is hereby incorporated by reference in its entirety. Said ASCII copy, created on Nov. 25, 2019, is named 423-003US_SL.txt and is 9,611 bytes in size.

TECHNICAL FIELD

The invention belongs to the field of bioengineering genes, and relates to a recombinant *Dermatophagoides pteronyssinus* type 1 allergen, and its coding gene and expression and purification method.

BACKGROUND ART

There are many kinds of dust mites, which are widely present in human living and working environments. The excreta, metabolites and mite bodies of dust mites have strong allergenicity. According to statistics, about 10% of the world's population is allergic to dust mites, and about 80% of extrinsic asthma is caused by dust mites.

At present, a crude extract of dust mite allergens is mainly used clinically to treat allergic diseases caused by dust mites. For example, *Dermatophagoides farinae* drops, named "Changdi", of Zhejiang Wolwopharma Co., which was marketed in 2006, is an extract of metabolic culture of *Dermatophagoides farinae*. Allergens of dust mites mainly exist in excreta and mite bodies; therefore, the extraction method takes a long time with a cumbersome process and a high cost. In addition, the composition of a natural allergen extract is very complicated, it is very difficult to make its components constant, and the natural allergen extract is easy to be contaminated by exogenous toxic substances and pathogenic microorganisms. Long-term use of a crude extract of dust mite allergens can lead to local reactions such as flush, swelling, induration and necrosis; and systemic reactions such as shock, edema, bronchospasm, urticaria, angioedema and systemic erythema. In addition, in the case that the crude extract is used for diagnosis, it is impossible to specifically determine the extent of the patient's response to each component of the allergens, which may lead to misdiagnosis.

The quality of the allergen is essential for the diagnosis and treatment of allergic diseases, and the allergen used for immunodiagnosis and immunotherapy should be a pure product rather than a crude extract. Recombinant allergens have the following advantages over crude extracts: (1) the recombinant allergens have a higher purity and contain no non-allergenic components, enzymes, enzyme inhibitors and toxic proteins as compared with the crude extracts; (2) the recombinant protein has a single composition, has good specificity, while the components in the crude extract are complex, the patient may only have reactions with some of the components of the crude extract, and the specificity is poor; (3) as compared with the natural extract, the recombinant allergen reduces IgE-bound antigenic epitopes and thus reduces IgE-mediated allergic reactions effectively, at the same time the domains of allergen necessary for T cell recognition are retained to result in better immunogenicity, thereby reducing the risk of immunotherapy and improving the desensitization therapy effect.

Allergens of dust mites are complex in composition, with more than 30 types, of which type 1 and type 2 allergens are the most important allergen components. At present, the most comprehensive study on *Dermatophagoides pteronyssinus* type 1 allergen (Der p1) is a study conducted by Japanese scholar Toshiro Takai et al. in 2005. The article indicates that it is necessary to add a propeptide of Der p1 protein (the propeptide of Der p1 is denoted as proDer p1) for expression of Der p1 in the *Pichia pastoris* system, otherwise Der p1 could not be expressed in an eukaryotic expression system. Then the propeptide was activated to obtain mature Der p1 protein which is consistent with the amino acid sequence of natural protein. In this article, the proDer p1 gene was not optimized results in low yield. Currently there are no further studies reported.

SUMMARY OF THE INVENTION

In order to overcome the above-mentioned shortcomings, the inventors optimize the proDer p1 gene in the *Pichia pastoris* expression system, and add an acting element to increase the expression of proDer p1 in molecular level, and the inventors surprisingly found that proDer p1 after gene optimization is expressed at a higher level as compared with the prior art; furthermore, the activation process of proDer p1 was further studied and optimized by the inventors, in which a more operational and scalable activation process was adopted. The purified mature Der p1 protein has a similar biological activity as the natural protein.

One object of the present invention is to provide a DNA sequence encoding proDer p1 protein, having a base sequence as shown in SEQ ID NO: 1. This sequence has been codon-optimized for the *Pichia pastoris* expression system, which is more conducive to expressing proDer p1 in *Pichia pastoris*.

Another object of the present invention is to provide proDer p1 protein having an amino acid sequence as shown in SEQ ID NO: 3.

Another object of the present invention is to provide Der p1 protein having an amino acid sequence as shown in SEQ ID NO: 4.

Another object of the present invention is to provide a vector comprising the above-mentioned optimized gene encoding proDer p1, preferably, the vector is pAO815, pPIC9, pPIC9K, pPIC3.5, pPIC3.5K, pPICZαA, B, C or pGAPZαA, B, C, more preferably pPIC3.5K, pPICZαA or pGAPZαA.

Another object of the present invention is to provide a *Pichia pastoris* strain comprising the above-mentioned vector, preferably, the *Pichia pastoris* strain is SMD1168, GS115, KM71, X33 or KM71H, more preferably strain KM71 or X33.

Preferably, there is 242 bp interval between the DNA sequence encoding the proDer p1 protein and the ATG of AOX1 of *Pichia pastoris*; the DNA sequence encoding the proDer p1 protein is preceded by an alpha-factor signal peptide and Kozak sequence GCCACCATGG (SEQ ID NO: 11).

Another object of the present invention is to provide a method for expressing the proDer p1 protein, comprising the steps of:

A constructing a vector comprising the above-mentioned gene encoding proDer p1;

B linearizing the vector of step A, transferring it into a *Pichia pastoris* strain, and culturing under a suitable condition;

C recovering and purifying the protein.

The above-mentioned vector is preferably pPIC3.5K, pPICZαA or pGAPZαA.

The above-mentioned *Pichia pastoris* strain is preferably a KM71 or X33 strain.

More preferably, the above-mentioned vector is pPICZαA, and the above-mentioned *Pichia pastoris* strain is strain X33.

Another object of the present invention is to provide a method for purifying a recombinant Der p1 protein, comprising the steps of:

A centrifuging the proDer p1 fermentation broth at a low temperature and a high speed to collect a supernatant, dialyzing the supernatant in a 5KD dialysis bag against a 25 mM sodium acetate buffer at pH 4.5 for 48 h, and filtering through a 0.45 μm filter membrane;

B the first step, cation chromatography, comprising equilibrating a chromatographic column with an equilibration buffer, passing the activated mature Der p1 fermentation broth in step A through a separation packing using a purification system, and then eluting with a gradient of an elution buffer to collect an elution peak, wherein the equilibration buffer is 50 mM sodium acetate at pH 4.5, and the elution buffer is 50 mM sodium acetate and 1.0 M sodium chloride at pH 4.5;

C the second step, comprising ultra-filtrating the Der p1 protein peak collected in step B with a 20 mM phosphate solution at pH 6.0, equilibrating a chromatographic column with an equilibration buffer, loading the ultra-filtrated Der p1 protein solution on an anion chromatography packing, and collecting a flow-through peak, wherein the equilibration buffer is 20 mM phosphate at pH 6.0; and D the third step, comprising adding ammonium sulfate to the flow-through peak in step C to the final concentration of 1.5 M, pH 6.0, equilibrating a chromatographic column with an equilibration buffer, loading a Der p1 sample on a hydrophobic chromatography packing, eluting with a gradient of an elution buffer, wherein equilibration buffer is 1.5 M ammonium sulfate and 20 mM phosphate at pH 6.0, and the elution buffer is 20 mM phosphate at pH 6.0.

Another object of the present invention is to provide the use of the recombinant Der p1 protein in the preparation of a medicament for treating a dust mite allergic disease. The allergic disease is allergic rhinitis, allergic asthma, and the like.

The recombinant Der p1 protein of the present invention has a high expression level and has similar biological activity as the natural protein.

BRIEF DESCRIPTION OF THE DRAWINGS

Figure 1:
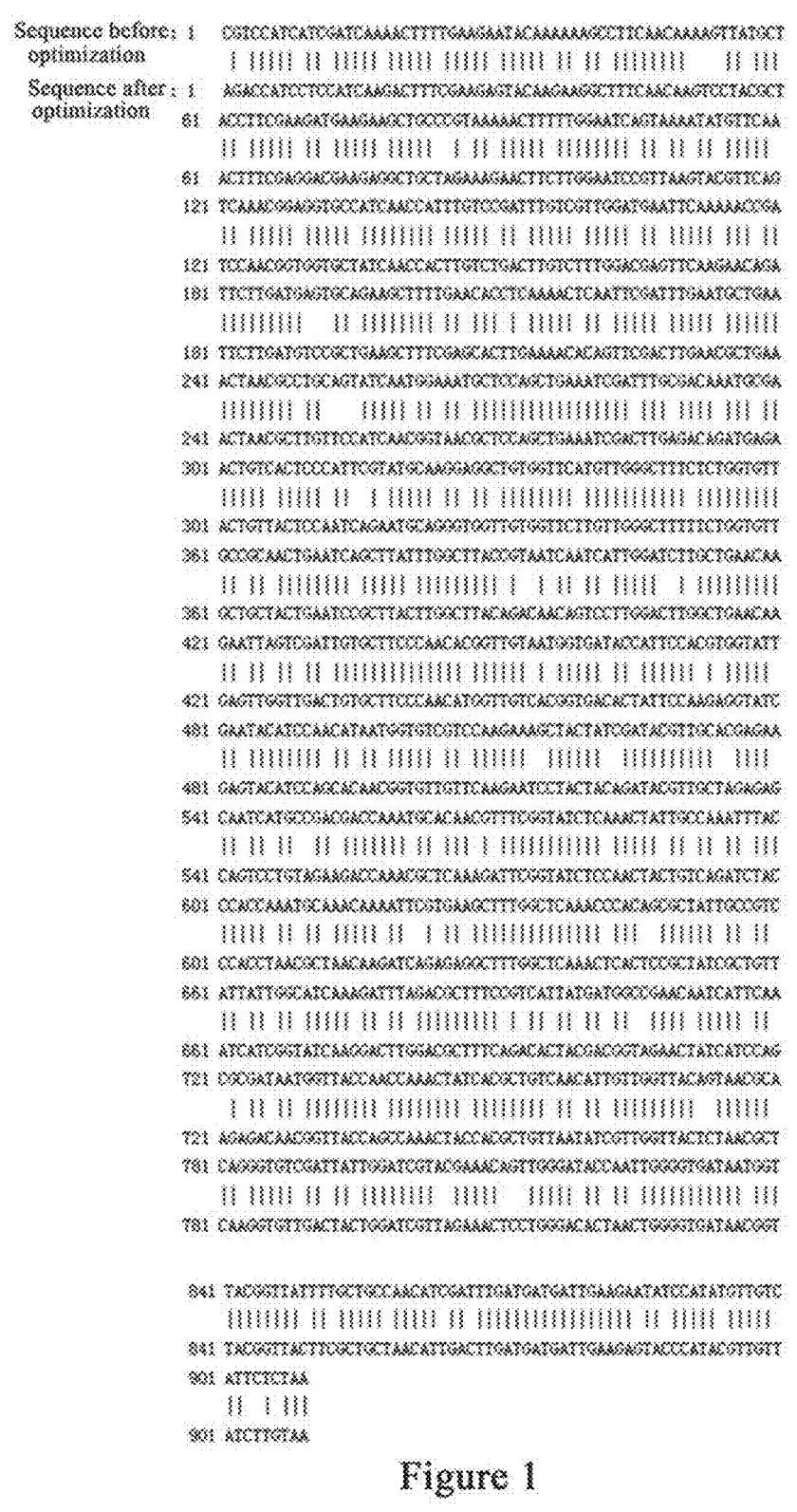

FIG. 1 is a comparison plot of sequences of the recombinant proDer p1 gene before and after optimization. FIG. 1 discloses SEQ ID NOS 2 and 1, respectively, in order of appearance.

The sequence before optimization corresponds to the nucleotide sequence of the natural proDer p1 gene; the sequence after optimization corresponds to the nucleotide sequence of the recombinant proDer p1 gene of the present invention, that is, the codon-optimized sequence.

FIGS. 2-*a* and 2-*b* show the CAI indices of the proDer p1 gene in the *Pichia pastoris* expression system before and after optimization.

FIG. 2-*a* shows that the CAI index of the nucleotide sequence of the natural proDer p1 gene in the *Pichia pastoris* expression system was calculated by a program to be 0.77. FIG. 2-*b* shows that the CAI index of the optimized proDer p1 codon of the present invention in the *Pichia pastoris* expression system is calculated by a program to be 0.90.

FIGS. 3-*a* and 3-*b* are optimal codon frequency distribution region plots of the proDer p1 gene in the *Pichia pastoris* expression host before and after codon optimization.

FIG. 3-*a* is an optimal codon frequency distribution region plot of the nucleotide sequence of natural proDer p1 gene in the *Pichia pastoris* system, and it can be seen from the figure that the occurrence percentage of low-utilization codon in the nucleotide sequence of natural proDer p1 gene is 9%. FIG. 3-*b* shows an optimal codon frequency distribution region plot of the optimized proDer p1 codon of the present invention in the *Pichia pastoris* system, and the occurrence rate of low-utilization codon in the sequence of optimized proDer p1 codon of the present invention is 0.

FIGS. 4-*a* and 4-*b* are average GC base content distribution region plots of the proDer p1 gene in the *Pichia pastoris* expression system before and after codon optimization.

FIG. 4-*a* shows that the average GC base content of the nucleotide sequence of the natural proDer p1 gene in the *Pichia pastoris* expression system is 41.68%. FIG. 4-*b* shows that the average GC base content of optimized proDer p1 codon of the present invention in the *Pichia pastoris* expression system is 46.22%.

FIG. 5 is an agarose gel electrophoretogram of a PCR product of the codon-optimized proDer p1 gene.

Lane 1 represents 500 bp DNA ladder; lane 2 represents a PCR product of the recombinant proDer p1 gene containing XhoI and XbaI restriction sites at both ends.

FIG. 6 is a diagram showing a construction process of the expression plasmid pPICZα-proDer p1 for codon-optimized proDer p1.

FIG. 7 is a diagram showing the identification of expression of the codon-optimized proDer p1 gene in the host engineering bacteria.

FIG. 7-*a* is a SDS-PAGE gel electrophoretogram of a supernatant of a solution of the host engineering strain containing the codon-optimized proDer p1 gene, after methanol-induced expression for one week. Lane 3 represents pre-stained protein loading markers in the range of 10-250 KD; and lanes 1-10 represent supernatants of cultured solutions of proDer p1 gene-positive monoclonal host engineering strains screened by Zeocin.

FIG. 7-*b* is a western blot plot of a supernatant of a solution of the host engineering strain containing the codon-optimized proDer p1 gene, after methanol-induced expression for one week. Lane 1 represents pre-stained protein loading markers in the range of 10-250 KD; and lanes 2-10 represent supernatants of cultured solutions of proDer p1 gene-positive monoclonal host engineering strains screened by Zeocin.

FIG. 8 shows a chromatogram of the supernatant of proDer p1 fermentation broth by cation chromatography of the first step, and a gel electrophoretogram.

FIG. 8-*a* is a chromatogram of the supernatant of proDer p1 fermentation broth by cation chromatography of the first step. FIG. 8-*b* is a gel electrophoretogram of samples collected by performing cation chromatography of the first step on the supernatant of proDer p1 fermentation broth, wherein lane 1 represents 11-100 KD non-pre-stained protein markers, lane 2 represents the supernatant of the proDer p1 fermentation broth before purification, lane 3 represents the flow-through liquid, and lanes 4-10 represent respective elution tubes.

FIG. 9 is a chromatogram of Der p1 protein by anion chromatography of the second step, and a gel electrophoretogram.

FIG. 9-a is a chromatogram of the supernatant of Der p1 fermentation broth by anion chromatography. FIG. 9-b is a gel electrophoretogram of samples collected by performing anion chromatography on the supernatant of Der p1 fermentation broth, wherein lane 1 represents 11-100 KD non-pre-stained protein markers, lane 2 represents the supernatant before purification of Der p1 protein, lane 3 represents the flow-through liquid of Der p1 protein, and lane 4 represents elution peaks of Der p1 protein.

FIG. 10 shows a chromatogram of Der p1 protein by hydrophobic chromatography of the third step and a gel electrophoretogram.

FIG. 10-a is a chromatogram of Der p1 protein by hydrophobic chromatography of the third step. FIG. 10-b is a gel electrophoretogram of samples collected by performing hydrophobic chromatography on Der p1 protein, wherein lane 1 represents 11-100KD non-pre-stained protein markers, and lane 2-8 represent respective elution tubes.

FIG. 11 is an dot-immunoblot identification plot of recombinant Der p1 and natural Der p1 with positive serum respectively, wherein nDerp1 represents the natural Der p1 protein, rDerp1 represents the recombinant Der p1 protein, and NC represents a PBS solution at pH 7.4.

FIG. 12 is an agarose gel electrophoretogram of a PCR-amplified GAP gene, wherein lane 1 represents 250 bp DNA ladder and lane 2 represents the GAP gene.

FIG. 13 is an agarose gel electrophoretogram for identifying T-vector positive clone of GAP gene through PCR, wherein lane 1 represents 250 bp DNA ladder, lanes 2-11 represent positive clones obtained by blue-white screening, and lane 12 represents a negative clone obtained by blue-white screening.

FIG. 14 is an agarose gel electrophoretogram of a PCR-amplified proDer p1 gene, wherein lane 1 represents 500 bp DNA ladder and lane 2 represents the proDer p1 gene.

FIG. 15 is an agarose gel electrophoretogram for identifying T-vector positive clone of proDer p1 gene through PCR, wherein lane 1 represents 500 bp DNA ladder, lanes 2 and 3 represent negative clones obtained by blue-white screening, lanes 4-16 represent positive clones obtained by blue-white screening, and lane 17 represents a positive control (proDer p1 gene).

FIG. 16 shows amplification curves of a standard plasmid.

FIG. 16-a shows amplification curves of the standard plasmid T-GAP, and FIG. 16-b shows amplification curves of the standard plasmid T-proDer p1.

FIG. 17 shows melting curves of a standard plasmid.

FIG. 17-a shows melting curves of the standard plasmid T-GAP, and FIG. 17-b shows melting curves of the standard plasmid T-proDer p1.

FIG. 18 shows a standard curve of a standard plasmid.

FIG. 18-a shows a standard curve of the standard plasmid T-GAP, and FIG. 18-b shows a standard curve of the standard plasmid T-proDer p1.

FIG. 19 shows amplification curves of samples to be tested.

FIG. 19-a shows amplification curves obtained when the samples to be tested are amplified with GAP-1 and GAP-2 as primers, and FIG. 19-b shows amplification curves obtained when the samples to be tested are amplified with 5'AOX and 3'AOX as primers.

FIG. 20 shows melting curves of samples to be tested.

FIG. 20-a shows melting curves obtained when the samples to be tested are amplified with GAP-1 and GAP-2 as primers, and FIG. 20-b shows melting curves obtained when the samples to be tested are amplified with 5'AOX and 3'AOX as primers.

DETAILED DESCRIPTION OF EMBODIMENTS

The invention is further illustrated below in conjunction with specific examples. It should be understood that the examples referred to are merely illustrative of the invention and are not intended to limit the scope of the present invention.

Example 1

Codon Optimization of Recombinant proDer p1

Based on the DNA sequence of proDer p1 disclosed in EMBL-EBI (ENA accession no. FM177224.1), as shown in SEQ ID No: 2, the inventors performed codon optimization of the gene to obtain the proDer p1 gene of the present invention of which the nucleotide sequence is as shown in SEQ ID No: 1 and the amino acid sequence is as shown in SEQ ID No: 3. Comparison of each parameter before and after codon optimization of the proDer p1 is as follows:

1. Codon Adaptation Index (CAI)

As can be seen from FIG. 2-a, the codon adaptation index (CAI) of the original proDer p1 gene in the *Pichia pastoris* expression system before codon optimization is 0.77. As can be seen from FIG. 2-b, the proDer p1 gene has a CAI index of 0.9 in the *Pichia pastoris* expression system after codon optimization. Usually, when CAI=1, it is considered that the gene is in the most ideal expression state in the expression system. The lower the CAI index, the worse the expression level of the gene in the host. Thus, it can be seen the gene sequence obtained by codon optimization can increase the expression level of the proDer p1 gene in the *Pichia pastoris* expression system.

2. Optimal Codon Usage Frequency (POP)

As can be seen from FIG. 3-a, based on the *Pichia pastoris* expression vector, the occurrence percentage of the low-utilization codon (codon with a utilization rate less than 40%) of the proDer p1 gene sequence is 9% before codon optimization. This unoptimized gene uses tandem rare codons that may reduce translation efficiency and even disintegrate a translation assembly. As can be seen from FIG. 3-b, the proDer p1 gene has a low utilization codon frequency of 0 in the *Pichia pastoris* system after codon optimization.

3. GC Base Content (GC Curve)

The ideal distribution region of GC content is 30%-70%, and any peak outside this region will affect transcription and translation efficiency to varying degrees. As can be seen from the comparison of the average GC base content distribution region plots of the proDer p1 gene in FIG. 4-a and FIG. 4-b, FIG. 4-a shows the average GC base content of the proDer p1 gene being 41.68%, and FIG. 4-b shows that the peaks of GC content appearing outside the 30%-70% region are removed after optimization, and finally the average GC base content of optimized proDer p1 is 46.22%.

Example 2

Construction of an Expression Plasmid Containing the proDer p1 Gene

A sequence of XhoI restriction site was introduced at the 5' end, and a sequence of XbaI restriction site was introduced at the 3' end of the codon-optimized proDer p1, and then full gene synthesis was performed. The synthesized gene fragment was constructed into the pUC57 plasmid supplied by GenScript (Nanjing) Co., Ltd., thereby obtaining a plasmid for long-term preservation, denoted as pUC57-proDer p1 plasmid.

PCR amplification was performed using the pUC57-proDer p1 plasmid as a template, and primers of following sequences:

```
upstream primer (SEQ ID No: 5):
M13 F:
TGT AAA ACG ACG GCC AGT downstream primer (SEQ ID No: 6):
M13 R:
CAG GAA ACA GCT ATG AC
```

The total volume of the reaction was 50 µL, in which 2.5 µL of each primer at a concentration of 10 µmol/L was added, 1 µL of dNTP at a concentration of 10 mmol/L was added, and 0.5 µL DNA polymerase being Q5 (#M0491L, purchased from New England BioLabs) at 2 U/µL was added. The reaction conditions were 98° C. for 5 seconds, 55° C. for 45 seconds, and 72° C. for 30 seconds. After 25 cycles, the product was analyzed by 1.0% agarose gel electrophoresis. The results showed that the product size was consistent with the expected size (1000 bp) (results as shown in FIG. 5). The product was digested with XhoI (#R0146S, purchased from New England BioLabs) and XbaI (#R01445S, purchased from New England BioLabs), respectively, and electrophoresed on 1% agarose gel to obtain a gene product, which was purified using a DNA gel recovery kit (DP214, purchased from Tiangen Biotech (Beijing) Co., Ltd.). The purified product was ligated to pPICZαA plasmid (V173-20, purchased from Invitrogen) with T4 ligase (#M0202S, purchased from New England BioLabs), and transformed into DH5α competent cells (CB101, purchased from Tiangen Biotech (Beijing) Co., Ltd.) and cultured in an LB solid medium containing bleomycin (purchased from Invitrogen) at 37° C. overnight. On the second day, the positive clones were picked and sequenced, and the sequence was found identical to the expected sequence by alignment, thereby obtaining the expression plasmid of codon-optimized proDer p1, denoted as pPICZα-proDer p1 (the plasmid construction was as shown in FIG. 6).

Example 3

Construction of a *Pichia Pastoris* Host Engineering Strain Containing a Recombinant proDer p1 Gene Formulation of YPDS solid medium: the medium was formulated according to the instructions of Easy Select*Pichia* Expression Kit, Invitrogen, comprising 10 g/L yeast extract, 20 g/L peptone, 20 g/L glucose, 15 g/L agarose, and 182 g/L sorbitol.

1. Construction of a Host Engineering Strain Containing Codon-Optimized proDer p1

Electrocompetent cells were prepared according to the method of instructions of Easy Select*Pichia* Expression Kit, Invitrogen. The plasmid pPICZα-proDer p1 obtained in Example 2 was linearized with Sac I restriction endonuclease (#R0156S, purchased from New England Biolabs), and precipitated with ethanol. The linearized vector was electrotransformed into competent cells of *Pichia pastoris* X33. The cells were plated on YPDS solid media and cultured at 30° C. until the transformants grew.

Example 4

Inducible Expression and Identification of Engineering Strains Containing Codon-Optimized proDer p1 Gene Formulation of BMGY medium: the medium was formulated according to the instructions of Easy Select*Pichia* Expression Kit, Invitrogen, comprising 10 g/L yeast extract, 20 g/L peptone, 3 g/L $K_2HPO_4$, 11.8 g/L $KH_2PO_4$, 13.4 g/L YNB, $4\times10^{-4}$ g/L biotin, and 10 g/L glycerin.

Formulation of BMMY medium: the medium was formulated according to the instructions of Easy Select*Pichia* Expression Kit, Invitrogen, comprising 10 g/L yeast extract, 20 g/L peptone, 3 g/L $K_2HPO_4$, 11.8 g/L $KH_2PO_4$, 13.4 g/L YNB, $4\times10^{-4}$ g/L biotin, and 5 mL/L methanol.

1. Methanol-Induced Expression of an Engineering Strain of Codon-Optimized proDer p1

The host monoclonal engineering strain obtained in Example 3 was picked into a 5 mL BMGY medium and cultured in a 50 mL sterile centrifuge tube at 30° C. and 220 rpm until $OD_{600}$ reaches 1.0-2.0. 1 mL of the culture was stored, and the remaining strain solution was resuspended and transferred to BMMY for induced expression at a small scale, and methanol was supplemented every 24 hours to a final concentration of 1%. One week later, the supernatant of the strain solution was collected by centrifugation, and analyzed by SDS-PAGE gel electrophoresis and Western blotting. Brightness of expressed product bands was observed. FIGS. 7-*a* and 7-*b* are plots of identification of induced expression of gene engineering strains containing Der p1. As seen from FIGS. 7-*a* and 7-*b*, the proDer p1 protein was significantly expressed in the engineering strain.

Example 5

Purification of Recombinant Der p1 Protein

The Der p1 constructed in this invention is obtained mainly by ion exchange and hydrophobic chromatography purification methods. HiTrap SP FF, HiTrap Q FF, and HiTrap Phenyl HP were selected as the chromatographic packings. The specific steps are as follows:

1. Pretreatment of the Fermentation Broth by Impurity Removal

The fermentation broth of host engineering strain containing proDer p1 obtained according to Example 4 was centrifuged by centrifugation at a low temperature at 12000 rpm for 15 minutes to collect a supernatant, and the supernatant was dialyzed in a 5 KD dialysis bag against a 25 mM sodium acetate buffer at pH 4.5 for 48 h, and filtered through a 0.45 µm filter membrane to obtain a supernatant of the treated fermentation broth.

2. Cation Exchange Chromatography

The treated fermentation broth of the previous step was loaded on a SPFF cation exchange chromatographic column, wherein the equilibration buffer was 50 mM NaAc at pH 4.5, the elution buffer was 50 mM NaAc and 1.0 M NaCl at pH 4.5, isocratic elution was performed at 12%, 25% and 100%, and the sample peaks were mainly concentrated at the 25% elution peak. FIG. 8-*a* is an ion exchange purification chromatogram of Der p1, and FIG. 8-*b* is an SDS-PAGE analysis plot of Der p1 after ion exchange chromatography.

3. Anion Exchange Chromatography

The Der p1 protein peak purified in the previous step was collected, and the sample was ultrafiltered with a 20 mM $NaH_2PO_4$ solution at pH 6.0, and loaded on a HiTrap Q FF chromatography packing. The equilibration buffer was 20 mM $NaH_2PO_4$ at pH 6.0, and the elution buffer was 20 mM $NaH_2PO_4$ and 1.0 M NaCl at pH 6.0. The flow-through peak of Der p1 was collected. The flow-through peak of Der p1 protein was as shown in FIG. 9.

4. Hydrophobic Chromatography

The flow-through peak of Der p1 from the anion chromatography was collected, and ammonium sulfate was added to a final concentration of 1.5 M. The fermentation broth supernatant treated as above was loaded on a Phenyl HP chromatographic column The equilibration buffer was 20 mM $NaH_2PO_4$ and 1.5 M $(NH_4)_2SO_4$ at pH 6.0; the elution buffer was 20 mM $NaH_2PO_4$ at pH 6.0, isocratic elution was performed at 25%, 50%, 70%, and 100%, and the Der p1 protein is mainly concentrated at the 75% elution peak. FIG. 10-*a* is hydrophobic chromatography purification chromatogram of Der p1, and FIG. 10-*b* is an SDS-PAGE analysis plot of Der p1 after hydrophobic chromatography. The yield of target protein per liter of fermentation broth is as high as 200 mg or more.

Example 6

Analysis of Der p1 Protein Activity

The purified Der p1 protein was dialyzed against a PBS buffer at pH 7.4, and the protein concentration was determined by a BCA protein concentration assay kit (Cat No: 23225, purchased from Pierce), and fold-diluted to 250 ng, 125 ng, 62.5 ng, 31.25 ng, and 15.625 ng. Using the dot immunoblotting method, the obtained solution was detected for the reactivity with sera of patients allergic to *Dermatophagoides pteronyssinus* by comparing with natural Der p2 as the control. FIG. 11 shows a dot immunoblot plot of recombinant Der p1 and natural Der p1 (NA-DP1-1, purchased from Indoor Biotechnologies) with positive serum, and the results indicate that the recombinant Der p1 has substantially identical reactivity with the sera as compared with the natural Der p1, showing that the recombinant Der p1 has a similar biological activity as the natural Der p1.

Example 7

Determination of Gene Copy Number of Recombinant proDer p1 Engineering Strain 1. Inoculation in X33 strain: the strains were cultured in YPD media for 24 h, the X33 genome was extracted by a genomic extraction kit (purchased from Tiangen Biotech (Beijing) Co., Ltd.), and GAP gene was amplified using the X33 genome as a template, and GAP-1 and GAP-2 as primers of which the sequences are as follows:

```
upstream primer (SEQ ID No: 7)
GAP-1:
GGTATTAACGGTTTCGGACGTATTG downstream primer (SEQ ID No: 8)
GAP-2:
GATGTTGACAGGGTCTCTCTCTTGG
```

The total volume of the reaction was 50 μL, in which 2.5 μL of each primer at a concentration of 10 μmol/L was added, 1 μL of dNTP at a concentration of 10 mmol/L was added, and 0.5 μL DNA polymerase being Taq DNA Polymerase (M0267S, purchased from New England BioLabs) at 2 U/μL was added. The reaction conditions were 94° C. for 10 minutes, 94° C. for 30 seconds, 55° C. for 30 seconds, 68° C. for 60 seconds, and 68° C. for 5 minutes. After 30 cycles, the product was analyzed by 1.0% agarose gel electrophoresis. The results showed that the product size was consistent with the expected size (400 bp) (results as shown in FIG. 12). The obtained gene product was purified by DNA gel recovery kit (DP214, purchased from Tiangen Biotech (Beijing) Co., Ltd.) and ligated into pGM-T vector kit (VT202-01, purchased from Tiangen Biotech (Beijing) Co., Ltd.). The Top10 competent cells (CB101, purchased from Tiangen Biotech (Beijing) Co., Ltd.) were transformed with the vector, and cultured at 37° C. overnight on blue-white screening media. On the next day, white clones were picked and identified by PCR for which the primers used were GAP-1 and GAP-2. The PCR reaction conditions were consistent with the above-mentioned conditions. The obtained product was analyzed by 1.0% agarose gel electrophoresis, and the results showed that the product size is consistent with the expected size (400 bp) (results as shown in FIG. 13). The positive clones were sent to GenScript (Nanjing) Co., Ltd. for sequencing, and the sequence was found completely identical to the expected sequence by alignment, thereby obtaining the T vector clone of GAP gene, denoted as T-GAP. The T-GAP clone having a correct sequence was inoculated in an LB liquid medium at 37° C. overnight, and the plasmid was extracted (using a plasmid mini-extract kit DP103, purchased from Tiangen Biotech (Beijing) Co., Ltd.) to obtain a standard plasmid for real-time quantitative PCR.

2. The proDer p1 gene was amplified using the pPICZα-proDer p1 plasmid of Example 2 as a template, and 5' AOX and 3' AOX primers with the following sequences:

```
upstream primer (SEQ ID No: 9):
5' AOX:
GACTGGTTCCAATTGACAAGC downstream primer (SEQ ID No: 12):
3' AOX:
GGCAAATGGCATTCTGACAT
```

The total volume of the reaction was 50 μL, in which 2.5 μL of each primer at a concentration of 10 μmol/L was added, 1 μL of dNTP at a concentration of 10 mmol/L was added, and 0.5 μL DNA polymerase being Taq DNA Polymerase (#M0267S, purchased from New England BioLabs) at 2 U/μL was added. The reaction conditions were 94° C. for 10 minutes, 94° C. for 30 seconds, 49° C. for 30 seconds, and 68° C. for 60 seconds, and 68° C. for 5 minutes. After 30 cycles, the product was analyzed by 1.0% agarose gel electrophoresis. The results showed that the product size was consistent with the expected size (1500 bp) (results as shown in FIG. 14). The obtained gene product was purified by DNA gel recovery kit (DP214, purchased from Tiangen Biotech (Beijing) Co., Ltd.) and ligated into pGM-T vector kit (VT202-01, purchased from Tiangen Biotech (Beijing) Co., Ltd.). The Top10 competent cells (CB104, purchased from Tiangen Biotech (Beijing) Co., Ltd.) were transformed with the vector, and cultured at 37° C. overnight on blue-white screening media. On the next day, white clones were picked and identified by PCR for which the primers used were 5'AOX and 3'AOX. The PCR reaction conditions were consistent with the above-mentioned conditions. The obtained product was analyzed by 1.0% agarose gel electrophoresis, and the results showed that the product size is consistent with the expected size (1500 bp) (results as shown in FIG. 15). The positive clones were sent to GenScript (Nanjing) Co., Ltd. for sequencing, and the sequence was found completely identical to the expected sequence by alignment, thereby obtaining the T vector clone of proDer p1, denoted as T-proDer p1. The T-proDer p1 clone having a correct sequence was inoculated in an LB liquid medium at 37° C. overnight, and the plasmid was extracted using a plasmid mini-extract kit (DP103, purchased from Tiangen Biotech (Beijing) Co., Ltd.) to obtain a standard plasmid for real-time quantitative PCR.

3. Calculation of Gene Copy Number:

The concentration (ng/μL) of the standard plasmid was determined by a nucleic acid microanalyzer (Nanodrop2000, ThermoFisher). Copy numbers of GAP and proDer p1 were calculated according to the following formula:

$$\text{Copies/u} = (6.02 \times 10^{23}) \times (\text{ng/μl} \times 10^{-9})/(\text{DNA length} \times 660)$$

4. Processing Samples to be Tested

The pPICZα-proDer p1-X33 engineering strain was inoculated in YPD liquid media at 30° C. overnight; and the genome was extracted the next day, and its concentration (ng/μL) and purity were determined by a nucleic acid quantitative microanalyzer.

5. Establishment of a Standard Curve

The standard plasmids of T-GAP and T-proDer p1 with known copy numbers were gradiently diluted to $10^8$, $10^7$, $10^6$, $10^5$, $10^4$, and $10^3$ copies/μl, respectively. The fluorescent quantitative PCR were performed using GAP-1 and GAP-2, 5' AOX and 3' AOX as primers, respectively. FIG. 16-a shows amplification curves of the standard plasmid T-GAP, FIG. 16-b shows amplification curves of the standard plasmid T-proDer p1, FIG. 17-a shows melting curves of the standard plasmid T-GAP, and FIG. 17-b shows melting curves of the standard plasmid T-proDer p1. Each gradient was assayed 3 times to verify the repeatability of the standard curve. Standard curves were established with the Ct values as the ordinate and the starting template copy numbers as the abscissa. FIG. 18-a shows a standard curve of the standard plasmid T-GAP, and FIG. 18-b shows a standard curve of the standard plasmid T-proDer p1.

6. Determination of Copy Number of ProDer p1 Gene in Recombinant Strains

The genome sample of extracted pPICZα-proDer p1-X33 was serially 10-fold-diluted to obtain four gradients of stock solution, $10^{-1}$, $10^{-2}$, and $10^{-3}$. Fluorescent quantitative PCR was performed using GAP-1 and GAP-2, 5' AOX and 3' AOX as primers, and each gradient was assayed three times. FIG. 19-a shows amplification curves of the samples to be tested with GAP-1 and GAP-2 as primers, FIG. 19-b shows amplification curves of the samples to be tested with 5' AOX and 3' AOX as primers, FIG. 20-a shows melting curves of the samples to be tested with GAP-1 and GAP-2 as primers, and FIG. 20-b shows melting curves of the samples to be tested with 5' AOX and 3' AOX as primers. The GAP gene exists in *Pichia pastoris* in a single copy. Therefore, the copy number of the GAP gene can be used to characterize the initial copy number of the genome in the template. The ratio of the copy number of the proDer p1 gene to the copy number of the GAP gene is the copy number of proDer p1 gene in the *Pichia pastoris* genome. Table 1 shows the detection results of copy number of the proDer p1 gene in the *Pichia pastoris* gene engineering strain, the detected copy number is between 4.98 and 5.46, and finally the copy number of the proDer p1 gene in the recombinant strain was averaged to eliminate the system error and determined to be 5.

TABLE 1

Results of copy number of proDer p1 in the genome detected by real-time fluorescent quantitative PCR

| DNA concentration | Average Ct value | | gene copy number ($10^N$) | | Copy number of proDer p1 gene in *Pichia pastoris* genome |
|---|---|---|---|---|---|
| | GAP gene | proDer p1 gene | GAP gene | proDer p1 gene | Copy number of the proDer p1 gene/copy number of the GAP gene |
| Stock solution | 17.41 | 23.18 | 7.02 | 5.87 | 5.46 |
| $10^{-1}$ | 20.29 | 24.32 | 6.11 | 5.59 | 5.31 |
| $10^{-2}$ | 23.63 | 24.35 | 5.10 | 5.41 | 5.22 |
| $10^{-3}$ | 28.23 | 24.39 | 3.82 | 5.28 | 4.98 |

Example 9

Analysis of the Acting Elements in the proDer p1 Genome

There is no stable additional plasmid in *Pichia pastoris*, the expression vector is homologously recombined with the host chromosome, and the exogenous gene expression framework is fully integrated into the chromosome to realize the expression of the exogenous gene; the typical *Pichia pastoris* expression vector contains a regulatory sequence of alcohol oxidase gene, and contains the main structures comprising AOX promoter, multiple cloning site, transcription termination and polyA formation gene sequence (TT), screening markers and the like. The promoter is a cis-element for gene expression regulation and an important element for the genetically engineered expression vector. The important role of the promoter at the transcriptional level determines the gene expression level.

The proDer p1 genome was extracted according to the method of Example 8, and the proDer p1 gene was amplified from the genome using 5' AOX and 3' AOX as primers according to the method in Step 2 of Example 8. The obtained samples were sent to GenScript (Nanjing) Co., Ltd. to detect the acting element before and after the proDer p1 gene which was inserted into the genome. The results of genome sequencing indicated that the proDer p1 gene expression framework was integrated into the chromosome of *Pichia pastoris* by a single cross-insertion, which enabled the proDer p1 gene to express the gene using the AOX promoter on the yeast chromosome, and thus the expression level was higher.

Generally, the closer the first ATG of the exogenous coding sequence to the ATG of AOX1, the better the expression effect. In the gene construction, the inventors chose an enzyme cleavage site closest to the ATG of AOX1, and found that the proDer p1 gene was away from ATG of AOX1 only by 242 bp. In addition, the alpha-factor signal peptide and Kozak sequence GCCACCATGG (SEQ ID NO: 11) were added in front of proDer p1 gene, and the signal peptide and the sequence can greatly improve transcription and translation efficiency and increase expression efficiency of proDer p1 gene in eukaryotes.

The invention claimed is:

1. A DNA sequence encoding a proDer p1 protein, said DNA having the base sequence as shown in SEQ ID NO: 1.

2. The DNA sequence of claim 1, wherein the DNA sequence is comprised in a vector pAO815, pPIC9, pPIC9K, pPIC3.5, pPIC3.5K, pPICZα A, B, C or pGAPZα A, B, C.

3. A DNA sequence of claim 2, wherein the vector is comprised in *Pichia pastoris* strain SMD1168, GS115, KM71, X33 or KM71H.

4. The DNA sequence of claim 3, wherein there is a 242 bp interval between the DNA sequence encoding proDer p1 protein and ATG of AOX1 on *Pichia pastoris*; and the DNA sequence encoding the proDer p1 protein is preceded by a sequence encoding an alpha-factor signal peptide and Kozak sequence GCCACCATGG.

* * * * *

SEQUENCE LISTING

<160> NUMBER OF SEQ ID NOS: 12

<210> SEQ ID NO 1
<211> LENGTH: 912
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
agaccatcct ccatcaagac tttcgaagag tacaagaagg ctttcaacaa gtcctacgct      60
actttcgagg acgaagaggc tgctagaaag aacttcttgg aatccgttaa gtacgttcag     120
tccaacggtg gtgctatcaa ccacttgtct gacttgtctt ggacgagtt caagaacaga      180 ttcttgatgt ccgctgaagc tttcgagcac ttgaaaacac agttcgactt gaacgctgaa     240
actaacgctt gttccatcaa cggtaacgct ccagctgaaa tcgacttgag acagatgaga     300
actgttactc caatcagaat gcagggtggt tgtggttctt gttgggcttt tctggtgtt     360 gctgctactg aatccgctta cttggcttac agacaacagt ccttggactt ggctgaacaa    420
gagttggttg actgtgcttc ccaacatggt tgtcacggtg acactattcc aagaggtatc    480
gagtacatcc agcacaacgg tgttgttcaa gaatcctact acagatacgt tgctagagag    540
cagtcctgta aagaccaaa cgctcaaaga ttcggtatct ccaactactg tcagatctac     600
ccacctaacg ctaacaagat cagagaggct ttggctcaaa ctcactccgc tatcgctgtt    660
atcatcggta tcaaggactt ggacgctttc agacactacg acggtagaac tatcatccag    720
agagacaacg gttaccagcc aaactaccac gctgttaata tcgttggtta ctctaacgct    780
caaggtgttg actactggat cgttagaaac tcctgggaca ctaactgggg tgataacggt    840
tacggttact cgctgctaa cattgacttg atgatgattg aagagtaccc atacgttgtt    900
atcttgcatt aa                                                        912
```

<210> SEQ ID NO 2
<211> LENGTH: 909
<212> TYPE: DNA
<213> ORGANISM: Dermatophagoides pteronyssinus

<400> SEQUENCE: 2

```
cgtccatcat cgatcaaaac ttttgaagaa tacaaaaaag ccttcaacaa aagttatgct      60
accttcgaag atgaagaagc tgcccgtaaa aacttttttgg aatcagtaaa atatgttcaa    120
tcaaacggag gtgccatcaa ccatttgtcc gatttgtcgt tggatgaatt caaaaaccga    180
ttcttgatga gtgcagaagc ttttgaacac ctcaaaactc aattcgattt gaatgctgaa    240
actaacgcct gcagtatcaa tggaaatgct ccagctgaaa tcgatttgcg acaaatgcga    300
actgtcactc ccattcgtat gcaaggaggc tgtggttcat gttgggcttt ctctggtgtt    360
gccgcaactg aatcagctta tttggcttac cgtaatcaat cattggatct tgctgaacaa    420
gaattagtcg attgtgcttc ccaacacggt tgtaatggtg ataccattcc acgtggtatt    480
gaatacatcc aacataatgg tgtcgtccaa gaaagctact atcgatacgt tgcacgagaa    540
caatcatgcc gacgaccaaa tgcacaacgt ttcggtatct caaactattg ccaaatttac    600
ccaccaaatg caaacaaaat tcgtgaagct ttggctcaaa cccacagcgc tattgccgtc    660
attattggca tcaagatttt agacgctttc cgtcattatg atggccgaac aatcattcaa    720
cgcgataatg gttaccaacc aaactatcac gctgtcaaca ttgttggtta cagtaacgca    780
```

```
cagggtgtcg attattggat cgtacgaaac agttgggata ccaattgggg tgataatggt    840
tacggttatt ttgctgccaa catcgatttg atgatgattg aagaatatcc atatgttgtc    900
attctctaa                                                            909
```

<210> SEQ ID NO 3
<211> LENGTH: 302
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Arg Pro Ser Ser Ile Lys Thr Phe Glu Glu Tyr Lys Lys Ala Phe Asn
1               5                   10                  15

Lys Ser Tyr Ala Thr Phe Glu Asp Glu Ala Ala Arg Lys Asn Phe
            20                  25                  30

Leu Glu Ser Val Lys Tyr Val Gln Ser Asn Gly Gly Ala Ile Asn His
        35                  40                  45

Leu Ser Asp Leu Ser Leu Asp Glu Phe Lys Asn Arg Phe Leu Met Ser
    50                  55                  60

Ala Glu Ala Phe Glu His Leu Lys Thr Gln Phe Asp Leu Asn Ala Glu
65                  70                  75                  80

Thr Asn Ala Cys Ser Ile Asn Gly Asn Ala Pro Ala Glu Ile Asp Leu
                85                  90                  95

Arg Gln Met Arg Thr Val Thr Pro Ile Arg Met Gln Gly Gly Cys Gly
            100                 105                 110

Ser Cys Trp Ala Phe Ser Gly Val Ala Ala Thr Glu Ser Ala Tyr Leu
        115                 120                 125

Ala Tyr Arg Gln Gln Ser Leu Asp Leu Ala Glu Gln Glu Leu Val Asp
    130                 135                 140

Cys Ala Ser Gln His Gly Cys Asn Gly Asp Thr Ile Pro Arg Gly Ile
145                 150                 155                 160

Glu Tyr Ile Gln His Asn Gly Val Val Gln Glu Ser Tyr Tyr Arg Tyr
                165                 170                 175

Val Ala Arg Glu Gln Ser Cys Arg Arg Pro Asn Ala Gln Arg Phe Gly
            180                 185                 190

Ile Ser Asn Tyr Cys Gln Ile Tyr Pro Pro Asn Ala Asn Lys Ile Arg
        195                 200                 205

Glu Ala Leu Ala Gln Thr His Ser Ala Ile Ala Val Ile Ile Gly Ile
    210                 215                 220

Lys Asp Leu Asp Ala Phe Arg His Tyr Asp Gly Arg Thr Ile Ile Gln
225                 230                 235                 240

Arg Asp Asn Gly Tyr Gln Pro Asn Tyr His Ala Val Asn Ile Val Gly
                245                 250                 255

Tyr Ser Asn Ala Gln Gly Val Asp Tyr Trp Ile Val Arg Asn Ser Trp
            260                 265                 270

Asp Thr Asn Trp Gly Asp Asn Gly Tyr Gly Tyr Phe Ala Ala Asn Ile
        275                 280                 285

Asp Leu Met Met Ile Glu Glu Tyr Pro Tyr Val Val Ile Leu
    290                 295                 300
```

<210> SEQ ID NO 4
<211> LENGTH: 222
<212> TYPE: PRT
<213> ORGANISM: Dermatophagoides pteronyssinus

<400> SEQUENCE: 4

```
Thr Asn Ala Cys Ser Ile Asn Gly Asn Ala Pro Ala Glu Ile Asp Leu
1               5                   10                  15

Arg Gln Met Arg Thr Val Thr Pro Ile Arg Met Gln Gly Gly Cys Gly
            20                  25                  30

Ser Cys Trp Ala Phe Ser Gly Val Ala Ala Thr Glu Ser Ala Tyr Leu
        35                  40                  45

Ala Tyr Arg Gln Gln Ser Leu Asp Leu Ala Glu Gln Glu Leu Val Asp
    50                  55                  60

Cys Ala Ser Gln His Gly Cys His Gly Asp Thr Ile Pro Arg Gly Ile
65                  70                  75                  80

Glu Tyr Ile Gln His Asn Gly Val Val Gln Glu Ser Tyr Tyr Arg Tyr
                85                  90                  95

Val Ala Arg Glu Gln Ser Cys Arg Arg Pro Asn Ala Gln Arg Phe Gly
            100                 105                 110

Ile Ser Asn Tyr Cys Gln Ile Tyr Pro Pro Asn Ala Asn Lys Ile Arg
        115                 120                 125

Glu Ala Leu Ala Gln Thr His Ser Ala Ile Ala Val Ile Ile Gly Ile
130                 135                 140

Lys Asp Leu Asp Ala Phe Arg His Tyr Asp Gly Arg Thr Ile Ile Gln
145                 150                 155                 160

Arg Asp Asn Gly Tyr Gln Pro Asn Tyr His Ala Val Asn Ile Val Gly
                165                 170                 175

Tyr Ser Asn Ala Gln Gly Val Asp Tyr Trp Ile Val Arg Asn Ser Trp
            180                 185                 190

Asp Thr Asn Trp Gly Asp Asn Gly Tyr Gly Tyr Phe Ala Ala Asn Ile
        195                 200                 205

Asp Leu Met Met Ile Glu Glu Tyr Pro Tyr Val Val Ile Leu
        210                 215                 220
```

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
tgtaaaacga cggccagt                                                 18

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
caggaaacag ctatgac                                                  17

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
ggtattaacg gtttcggacg tattg                                    25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gatgttgaca gggtctctct cttgg                                    25

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gactggttcc aattgacaag c                                        21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gcaaatggca ttctgacatc c                                        21

<210> SEQ ID NO 11
<211> LENGTH: 10
<212> TYPE: DNA
<213> ORGANISM: Unknown
<220> FEATURE:
<223> OTHER INFORMATION: Description of Unknown:
      Kozak sequence

<400> SEQUENCE: 11
gccaccatgg                                                     10

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggcaaatggc attctgacat                                          20